(12) United States Patent
Parikh et al.

(10) Patent No.: US 6,465,016 B2
(45) Date of Patent: *Oct. 15, 2002

(54) CYCLOSPORIINE PARTICLES

(75) Inventors: Indu Parikh, Durham, NC (US);
Robert A. Snow, West Chester, PA (US)

(73) Assignee: Research Triangle Pharmaceuticals, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/750,218

(22) Filed: Dec. 29, 2000

(65) Prior Publication Data

US 2002/0013271 A1 Jan. 31, 2002

Related U.S. Application Data

(63) Continuation-in-part of application No. 09/218,080, filed on Dec. 22, 1998, now Pat. No. 6,228,399, which is a continuation-in-part of application No. 08/701,483, filed on Aug. 22, 1996, now abandoned.

(51) Int. Cl.$^7$ .......................... A61K 9/14; A61K 47/32; S01N 33/92
(52) U.S. Cl. ...................... 424/489; 424/486; 514/772.4
(58) Field of Search ................................ 424/489, 486, 424/490, 502; 514/772.4

(56) References Cited

U.S. PATENT DOCUMENTS

| | | |
|---|---|---|
| 4,411,933 A | 10/1983 | Samejima et al. |
| 4,725,442 A | 2/1988 | Haynes |
| 4,963,367 A | 10/1990 | Ecanow |
| 4,990,337 A | 2/1991 | Kurihara et al. |
| 5,091,187 A | 2/1992 | Haynes |
| 5,091,188 A | 2/1992 | Haynes |
| 5,326,552 A | 7/1994 | Na et al. |
| 5,364,633 A | 11/1994 | Hill et al. |
| 5,389,377 A | 2/1995 | Chagnon et al. |
| 5,447,710 A | 9/1995 | Na et al. |
| 5,527,537 A | 6/1996 | Dietl |
| 5,576,016 A | 11/1996 | Anselem et al. |
| 5,589,455 A | 12/1996 | Woo |
| 5,603,951 A | 2/1997 | Woo |
| 5,639,474 A | 6/1997 | Woo |
| 5,662,932 A | * 9/1997 | Amselem et al. ........... 424/450 |

FOREIGN PATENT DOCUMENTS

| | | |
|---|---|---|
| DE | 34 21 468 A1 | 12/1985 |
| EP | 0 330 532 | 8/1989 |
| EP | 0 391 369 | 10/1990 |
| EP | 0 570 829 | 11/1993 |
| EP | 0 601 618 A2 | 6/1994 |
| EP | 0 602 700 A2 | 6/1994 |
| EP | 0 724 877 A1 | 8/1996 |
| EP | 0 757 911 A1 | 2/1997 |
| FR | 2 617 047 | 12/1988 |
| WO | WO 94/20072 | 9/1994 |
| WO | WO 96/21439 | 7/1996 |
| WO | WO 97/14407 | 4/1997 |
| WO | 200130372 | * 5/2001 |

* cited by examiner

*Primary Examiner*—Thurman K. Page
*Assistant Examiner*—Blessing Fubara
(74) *Attorney, Agent, or Firm*—Nixon & Vanderhye P.C.

(57) ABSTRACT

Pharmaceutical compositions containing solid cyclic oligopeptide cyclosporine microparticles are prepared by applying energy input to solid cyclic oligopeptide cyclosporine in the presence of phospholipid and one or more non-ionic, anionic or cationic second surface modifiers. The microparticles consist essentially of a solid cyclic oligopeptide cyclosporine core coated with a combination of phospholipid and at least one second surface modifier. The combination of phospholipid and second surface modifier(s) provide volume-weighted mean particle size values of solid cyclic oligopeptide cyclosporine particles that are about 50% smaller than cyclic oligopeptide cyclosporine particles produced in the presence of the phospholipid and without the presence of the second surface modifier(s) using the same energy input.

22 Claims, No Drawings

CYCLOSPORIINE PARTICLES

This application is a continuation-in-part of Ser. No. 08/701,483 filed Aug. 22, 1996 now abandoned.

This invention relates to compositions and procedures that yield sub-micron and micron stable particles of solid water-insoluble or solid poorly soluble drugs such as cyclic oligopeptide cyclosporine or other industrially useful insoluble compounds. The compositions of this invention include combinations of natural or synthetic phospholipids, and one or more non-ionic, anionic or cationic second surfactants, which are also referred to interchangeably herein as second surface modifiers, coated or adhered onto the surfaces of the water-insoluble-compound particles, each of which contains a core of solid compound. The combination of phospholipids and one or more second surfactants (or second surface modifiers) allows the formation and stabilization of the sub-micron and micron size compound particles via hydrophilic, lipophilic and electrostatic interactions and therefore prevents these particles from aggregation or flocculation.

BACKGROUND OF THE INVENTION

Cyclic oligopeptide cyclosporine, a drug, is a potent immunosuppressive agent that in animals prolongs survival of allogeneic transplants involving skin, kidney, liver, heart, pancreas, bone marrow, small intestine, and lung. Cyclosporine has been demonstrated to suppress some humoral immunity and to a greater extent, cell-mediated immune reactions such as allograft rejection, delayed hypersensitivity, experimental allergic encephalomyelitis, Freund's adjuvant arthritis, and graft vs. host disease in many animal species for a variety of organs. Cyclosporin is useful in these and other indications. For example, cyclosporine is useful as an immunosuppressive agent in humans. Cyclosporine has been used in immunosuppressive therapy and management of organ transplant recipients to prevent rejection of transplanted organs (e.g., skin, pancreas, bone marrow, small intestine, lung, kidney, liver, heart), in immunosuppressive therapy and management of rheumatoid arthritis, and immunosuppressive therapy and management of psoriasis.

The oral bioavailability of cyclosporine in human patients in available cyclosporine dosage forms is not complete, varies among patients in a patient population, and varies with the formulation, varies when food is taken by a patient proximal to the time of administration of a cyclosporine dosage form to or by the patient. When the level of cyclosporine received by a patient is not well controlled, the patient can experience undesired side effects that include organ rejection when concentrations achieved are too low. When the level of cyclosporine received by a patient is too high, renal dysfunction, nephrotoxicity, hepatotoxicity, and systemic hypertension can result.

Cyclosporines are generally cyclic oligopeptides, and examples of this class of drug are described in The Merck Index, Twelfth Edition, page 464–465 which is herein incorporated by reference. Cyclosporins are a group of nonpolar cyclic oligopeptides with immunosuppressant activity. Cyclosporins can be naturally derived such as produced by and isolated from fungi, or they can be prepared synthetically. The solid cyclic oligopeptide cyclosporin A is a white solid which in one crystalline form appears as white prismatic needles with a melting point of 148–152° C. when crystallized from acetone. This cyclic oligopeptide cyclosporine A is soluble in alcohol but is poorly soluble in water and aliphatic hydrocarbons, and it does not have an affinity for either water or aliphatic hydrocarbons.

Cyclosporine A is commercially available in alcohol solution as Neoral® soft gelatin capsules and as Neoral® oral solution, oral formulations of cyclosporine that rapidly form microemulsions in an aqueous environment. Currently available Neoral® Soft Gelatin cyclosporine capsules for microemulsion are available in 25 mg and 100 mg strengths that contain 11.9% v/v (9.5% wt/vol) alcohol, USP dehydrated. Inactive ingredients in the formulation include corn-oil-mono-di-triglycerides, polyoxyl 40 hydrogenated castor oil NF, DL-(alpha)-tocopherol USP, gelatin NF, glycerol, iron oxide black, propylene glycol USP, titanium dioxide USP, and carmine. Currently available Neoral® cyclosporine oral solution for microemulsion is available in 50 mL bottles with each milliliter containing 100 mg/mL cyclosporine and 11.9% v/v (9.5% wt/vol.) alcohol, USP dehydrated. Inactive ingredients include corn oil-mono-di-triglycerides, polyoxyl 40 hydrogenated castor oil NF, DL-(alpha)-tocopherol USP, and propylene glycol USP.

Cyclosporine is also commercially available in alcohol solution as Sandimmune® soft gelatin capsules, as Sandimmune® oral solution, USP, and as Sandimmune® injection. Inactive ingredients present in these formulations include corn oil, olive oil, gelatin, glycerol, Labrafil M 2125 CS (polyoxyethylated glycolysed glycerides), Labrafil M 1944 CS (polyoxyethylated oleic glycerides), sorbitol, and Cremophor EL (polyoxyethylated castor oil). Cremophor® EL (polyoxyethylated castor oil) is known to cause hyperlipemia and electrophoretic abnormalities of lipoproteins. Cremophor® EL (polyoxyethylated castor oil) contained in currently available concentrate for intravenous infusion can cause phthalate stripping from PVC.

When currently available formulations are compared, Neoral® dosage forms exhibit increased bioavailability of cyclosporine in comparison to Sandimmune® dosage forms. These currently available dosage forms are not bioequivalent and thus cannot be used interchangeably. For a given trough concentration, cyclosporine exposure will be greater with Neoral® than with Sandimmune®.

Neoral dosage forms can carry up to about 100 mg/mL of cyclosporine and the dosage form can be relatively large.

The absolute bioavailability of cyclosporine administered as Sandimmune® is dependent on the patient population, and is estimated to be less than 10% in liver transplant patients and as great as 89% in some renal transplant patients for which cyclosporine therapy is indicated. In studies of renal transplant, rheumatoid arthritis and psoriasis patients, the mean cyclosporine AUC is known to be approximately 20% to 50% greater and the peak blood cyclosporine concentration ($C_{max}$) approximately 40% to 106% greater following administration of Neoral® compared to following administration of Sandimmune®. The dose normalized AUC in de novo liver transplant patients administered Neoral® 28 days after transplantation is known to be 50% greater and $C_{max}$ 90% greater than in those patients administered Sandimmune®. In another indication for cyclosporine therapy, AUC and $C_{max}$ are also increased (Neoral® relative to Sandimmune®) in heart transplant patients.

Following oral administration of Neoral®, the time to peak blood cyclosporine concentrations ($T_{max}$) currently ranges from 1.5–2.0 hours. The administration of food with Neoral® is known to decrease the cyclosporine AUC and $C_{max}$. A high fat meal (669 kcal, 45 grams fat) consumed within one-half hour before Neoral® administration is known to decrease the AUC by 13% and $C_{max}$ by 33%. The effects of a low fat meal (667 kcal, 15 grams fat) are known to be similar.

A number of drugs are known to increase in vivo levels of cyclosporine when administered to a patient at a time proximal to administration of cyclosporin. These include diltiazem, danazol, nicardipine, bromocriptine, verapamil, metoclopramide, erythromycin, methylprednisolone, ketoconazole, fluconazole, and itraconazole.

A number of drugs are known to decrease in vivo levels of cyclosporine when administered to a patient at a time proximal to administration of cyclosporin. These include rifampin, phenobarbital, phenytoin and carbamazepine.

It would be useful to have a dosage formulation of cyclic oligopeptide cyclosporine that provides an amount of cyclic oligopeptide cyclosporine to a patient in need of treatment by cyclic oligopeptide cyclosporine who has recently ingested a high fat meal or a low fat meal that is comparable to the amount of cyclic oligopeptide cyclosporine provided to the same patient in a fasted state. Preferably, these fed-fasted comparable amounts will be within 80% of each other, more preferably within 90% or each other, and most preferably with 95% of each other, thereby minimizing the effect of food or obviating it altogether.

Following oral administration of currently available dosage forms of cyclosporine, absorption of cyclosporine is known to be incomplete. The extent of absorption of cyclosporine is dependent on the individual patient, the patient population, and the formulation. The relationship between administered dose and exposure (area under the concentration versus time curve, AUC) is linear within the therapeutic dose range. Intersubject variability of cyclosporine exposure (AUC) when Neoral® or Sandimmune® is administered ranges from approximately 20% to 50% in renal transplant patients. This intersubject variability contributes to the need for individualization of the dosing regimen for optimal therapy. Intrasubject variability of AUC in renal transplant recipients (%CV) is known to be 9%-21% for Neoral® and 19%-26% for Sandimmune® when intrasubject variability of trough concentrations (%CV) is 17%-30% for Neoral® and 16%-38% for Sandimmune®.

There is thus a need for an improved dosage form of cyclic oligopeptide cyclosporine that offers an improved bioavailability and safety in a more compact dosage form.

There is also a critical need in the pharmaceutical and other biological based industries to formulate water-insoluble or poorly soluble drug substances such as solid cyclic oligopeptide cyclosporine or cyclosporin A into formulations for oral, injectable, inhalation and ophthalmic routes of delivery.

BRIEF DESCRIPTION OF THE INVENTION

This invention provides a pharmaceutical composition consisting of cyclic oligopeptide cyclosporine microparticles stabilized with a combination of phospholipid and at least one second surface modifier, wherein said microparticles are produced by applying an energy input to solid cyclic oligopeptide cyclosporine in the presence of said phospholipid and said second surface modifier, wherein said microparticles each consist essentially of a solid cyclic oligopeptide cyclosporine core coated with a combination of said phospholipid and said surface modifier, and wherein said surface modifier provides a volume-weighted mean particle size value of solid cyclic oligopeptide cyclosporine about 50% smaller than the volume-weighted mean particle size value of particles produced in the presence of said phospholipid and without the presence of said surface modifier using the same energy input.

The compositions of this invention can be in the form of suspensions, especially suspensions in an aqueous medium such as water, water for injection, buffered water, phosphate buffered saline, and other pharmaceutically acceptable aqueous media. Alternatively, the compositions of this invention can be in the form of dried powders which are substantially free of water, particularly at least 98% free of water. The powders can be further manipulated to form tablets, capsules, suspensions, creams, ointments, pills, suppositories, and other useful and pharmaceutically acceptable dosage forms.

In another aspect, this invention provides a pharmaceutical composition consisting of cyclic oligopeptide cyclosporine microparticles stabilized with a combination of phospholipid and at least one second surface modifier, wherein said microparticles are produced by applying an energy input to solid cyclic oligopeptide cyclosporine in the presence of said phospholipid and said second surface modifier; wherein said microparticles each consist essentially of a solid cyclic oligopeptide cyclosporine core coated with a combination of said phospholipid and said surface modifier; and wherein the second surface modifier is selected from the group consisting of non-ionic surface modifiers, anionic surface modifiers, and cationic surface modifiers; and wherein said surface modifier provides a volume-weighted mean particle size value of solid cyclic oligopeptide cyclosporine about 50% smaller than the volume-weighted mean particle size value of particles produced in the presence of said phospholipid and without the presence of said surface modifier using the same energy input.

Cyclic oligopeptide cyclosporins of this invention are water-insoluble or poorly water-soluble solid cyclic oligopeptides. The solid cyclic oligopeptide cyclosporins can be amorphous or crystalline, and are preferably crystalline. A preferred cyclic oligopeptide cyclosporine is cyclosporine A.

In one aspect of this invention, the cyclic oligopeptide cyclosporine can be an amorphous solid in the particle core. In another aspect of this invention, the cyclic oligopeptide cyclosporine can be a crystalline solid in the particle core. In yet another aspect of this invention, the cyclic oligopeptide cyclosporine can be a mixture of amorphous and crystalline solids in the same particle core. The cyclic oligopeptide cyclosporine is preferably a single stereoisomer, but it can also be a mixture of stereoisomers, a racemic mixture of stereoisomers, a diastereomeric mixture of isomers, or a combination of optical isomers of a single cyclic oligopeptide cyclosporine homologue.

Water-insoluble compounds are those having poor solubility in water, that is, <5 mg/ml at physiological pH (6.5–7.4). Preferably their water solubility is <1 mg/ml, more preferably <0.1 mg/ml. In one aspect, it is desirable that the drug is stable in water as a dispersion; otherwise a lyophilized or spray-dried solid form may be desirable.

As used herein, “micro” refers to a particle having diameter of from nanometers to micrometers. Microparticles, as used herein, refer to solid particles of irregular, non-spherical or spherical shapes and containing a solid core of solid drug such as a solid core of cyclic oligopeptide cyclosporine. Formulations containing these microparticles provide some specific advantages over the unformulated non-micronized drug particles, which include improved oral bioavailability of drugs that are poorly absorbed from the GI tract, development of improved injectable formulations that are currently available only in oral dosage form, improved less toxic injectable formulations that are currently prepared with organic solvents such as alcohol, improved sustained release of intramuscular injectable drugs that are currently administered through daily injection or constant infusion, and preparation of inhaled, ophthalmic formulation of drugs that otherwise could not be formulated for nasal or ocular use.

Current technology for delivering insoluble drugs as described in U.S. Pat. Nos. 5,091,188; 5,091,187 and 4,725,442 focuses on (a) either coating small drug particles with natural or synthetic phospholipids or (b) dissolving the drug in a suitable lipophilic carrier and forming an emulsion stabilized with natural or semisynthetic phospholipids. One of the disadvantages of these formulations is that certain drug particles in suspension tend to grow over time because of the dissolution and reprecipitation phenomenon known as the "Ostwald ripening" in which a particle can grow in size, sometimes substantially more than 50% of its original size.

U.S. Pat. No. 5,576,016 (Amselem et al.) entitled "Solid Fat Nanoemulsions as Drug Delivery Vehicles" discloses lipid-in-water emulsions for delivery of both fat-soluble and water-soluble drugs. Unlike the present invention in which the particles consist essentially of a solid particle core of cyclosporin that is coated with a combination of a phospholipid together with a second surface modifier, the emulsions of U.S. Pat. No. 5,576,016 have a lipid core surrounded by at least one phospholipid envelope as in a liposome. Fat-soluble drugs can be dissolved in the solid lipid core.

U.S. Pat. No. 5,336,507 discloses a composition of nanoparticles having a non-ionic surfactant as a surface modifier adsorbed on the surface of the particle and a charged phospholipid as a cloud point modifier present in an amount sufficient to increase the cloud point of the surface modifier. However, the charged phospholipid is not coated on the surface of the particles.

DETAILED DESCRIPTION OF THE INVENTION

The present invention describes compositions and methods for the preparation of submicron to micron size particles of solid cyclic oligopeptide cyclosporine wherein the particles are stabilized by a combination of one or more surface modifier(s) together with a phospholipid, and such combination of surface modifiers and phospholipid provides microparticles that are unexpectedly smaller, usually about 50% smaller, including sometimes more than 50% smaller, than particles of cyclosporine prepared with the same phospholipid in the absence of the surface modifier(s). This invention further describes how the growth of particle size of particles of solid cyclic oligopeptide cyclosporine is controlled or limited and how the rate of growth in particle size of solid cyclic oligopeptide cyclosporine particles is controlled or limited or reduced when a combination of surface modifier(s) together with a phospholipid is present in formulations such as suspensions of the particles versus when the phospholipid alone is present in formulations. Particles and formulations of particles of cyclic oligopeptide cyclosporine stabilized by a combination of one or more surface modifier(s) together with phospholipid exhibit enhanced storage stability over particles and formulations of particles of cyclic oligopeptide cyclosporine stabilized by the phospholipid in the absence of said one or more surface modifier(s).

In particular, this invention describes a pharmaceutical composition of cyclic oligopeptide cyclosporine microparticles produced by applying an energy input to solid cyclic oligopeptide cyclosporine in the presence of phospholipid and at least one second surface modifier(s), wherein said microparticles each consist essentially of a solid cyclic oligopeptide cyclosporine core coated with a combination of said phospholipid and said surface modifier(s), and wherein said surface modifier(s) provides a volume-weighted mean particle size value of solid cyclic oligopeptide cyclosporine about 50% smaller than the volume-weighted mean particle size value of particles produced in the presence of said phospholipid and without the presence of said surface modifier(s) using the same energy input.

This invention further describes a pharmaceutical composition consisting of cyclic oligopeptide cyclosporine microparticles stabilized with a combination of phospholipid and at least one second surface modifier, wherein said microparticles are produced by applying an energy input to solid cyclic oligopeptide cyclosporine in the presence of said phospholipid and said second surface modifier, wherein said microparticles each consist essentially of a solid cyclic oligopeptide cyclosporine core coated with a combination of said phospholipid and said surface modifier, and wherein said surface modifier provides a volume-weighted mean particle size value of solid cyclic oligopeptide cyclosporine about 50% smaller than the volume-weighted mean particle size value of particles produced in the presence of said phospholipid and without the presence of said surface modifier using the same energy input.

More particularly, this invention further describes a pharmaceutical composition consisting of cyclic oligopeptide cyclosporine microparticles stabilized with a combination of phospholipid and at least one second surface modifier, wherein said microparticles are produced by applying an energy input to solid cyclic oligopeptide cyclosporine in the presence of said phospholipid and said second surface modifier; wherein said microparticles each consist essentially of a solid cyclic oligopeptide cyclosporine core coated with a combination of said phospholipid and said surface modifier; and wherein the second surface modifier is selected from the group consisting of non-ionic surface modifiers, anionic surface modifiers, and cationic surface modifiers; and wherein said surface modifier provides a volume-weighted mean particle size value of solid cyclic oligopeptide cyclosporine about 50% smaller than the volume-weighted mean particle size value of particles produced in the presence of said phospholipid and without the presence of said surface modifier using the same energy input.

The use of a surface modifier or combination of surface modifiers in addition to one or more phospholipid is characterized by its ability to result in volume weighted mean particle size values that are (i) at least 50% and preferably about 50–90% smaller than what can be achieved using phospholipid alone without the use of a surface modifier with the same energy input, and (ii) provide compositions of cyclic oligopeptide cyclosporine that are resistant to particle size growth on storage. While resistance to solid cyclic oligopeptide cyclosporine particle size growth on storage was an objective of this invention we were surprised to observe a significant reduction in cyclic oligopeptide cyclosporine particle size with the addition of surface modifier. In order to achieve the advantages of the present invention it is necessary that the phospholipid and the surface modifier both be present at the time of particle size reduction or precipitation.

In another aspect, the present invention describes a pharmaceutical composition of cyclic oligopeptide cyclosporine microparticles produced by applying energy to solid cyclic oligopeptide cyclosporine in the presence of phospholipid and surface modifier(s), said microparticles consisting essentially of a solid cyclic oligopeptide cyclosporine core coated with a phospholipid and at least one surface modifier in which the surface modifier(s) provide volume-weighted mean particle size values of solid cyclic oligopeptide cyclosporine about 50% smaller than particles produced in the presence of a phospholipid and without the presence of the surface modifier(s) using the same energy input.

The present invention also describes a pharmaceutical composition of cyclic oligopeptide cyclosporine microparticles produced by applying energy to solid cyclic oligopeptide cyclosporine in the presence of phospholipid and one or more second surfactants, said microparticles consisting essentially of a solid cyclic oligopeptide cyclosporine core coated with a phospholipid and at least one non-ionic, anionic or cationic second surfactant, in which the second surfactant or second surfactants provide volume-weighted mean particle size values of solid cyclic oligopeptide cyclosporine about 50% smaller than particles produced in the presence of a phospholipid and without the presence of the second surfactant using the same energy input.

Another aspect of the present invention includes freeflowing powders of particles of poorly soluble or insoluble drug substances such as solid cyclic oligopeptide cyclosporine as well as solid dosage forms of these powders, for instance in the form of compressed tablets and the like. Surprisingly we have found that microparticulate formulations exhibit enhanced stability and bioavailability as illustrated in the data that follows. The size of the final dosage form is also significantly smaller than the currently marketed microemulsion forms of cyclosporine.

Although we do not wish to be bound by any particular theory, it appears that these surface modifiers generally, that is phospholipids and one or more second surfactant surface modifiers, adsorb to the surfaces of drug particles which contain a core of solid cyclic oligopeptide cyclosporine, and (a) convert lipophilic to hydrophilic surfaces with increased steric hindrance/stability, and (b) possibly modify zeta potential of surfaces with more charge repulsion stabilization. The concentrations of surface modifiers used in the process described here are normally above their critical micelle concentrations (CMC) and hence facilitate the formation of sub-micron to micron particles by stabilizing the particles.

Herein, surfactant and surface modifier are used interchangeably, and the term "surface modifier(s)" refers to one or more surface modifiers.

Phospholipid and surface modifier(s) are adsorbed onto the surfaces of drug particles containing a solid core of drug, particularly a solid core of solid cyclic oligopeptide cyclosporine, in sufficient quantity to retard drug particle growth, reduce drug average particle size from 5 to 100 μm to sub-micron and micron size particles by one or a combination of methods known in the art, such as sonication, homogenization, milling, microfluidization, precipitation or recrystallization or precipitation from supercritical fluid, and maintain sub-micron and micron size particles on subsequent storage as suspension or solid dosage form.

The concentration of phospholipid or surface modifier in the suspension or solid dosage form can be present in the range of 0.1 to 50%, preferably 0.2 to 20%, and more preferably 0.5 to 10%.

The formulations prepared by this invention are useful as pharmaceutical compositions and may be dried, e.g., by lyophilization, fluid or spray drying, evaporation, or other known methods, into powders optionally in the presence of excipients such as carbohydrates such as sugars (e.g., mannitol), salts such as buffering salts and salts that can produce isotonic formulations, dispersing aids, binders and the like, which dried powders can be resuspended or filled into capsules (e.g., hard gel or soft gel capsule dosage formulations) or converted into granules or tablets with the addition of binders such as polyvinylpyrrolidone and other excipients such as magnesium stearate and silica known in the art of tablet and capsule making.

In one aspect the pharmaceutical compositions are suitable for oral, inhalation, ocular, nasal or injectable administration. In another aspect, the pharmaceutical compositions are suitable for use in injectable form for intravenous, intra-arterial, intra-muscular, intradermal, subcutaneous, intra-articular, cerebrospinal, epidural, intracostal, intraperitoneal, intratumor, intrabladder, intra-lesion or subconjunctival administration.

Cyclic oligopeptide cyclosporine in the microparticles of the current invention as solid cores of cyclic oligopeptide cyclosporine can be dosed at levels ranging from 0.1 to 20 mg/kg/day, preferably from 0.5 to 15 mg/kg/day, and most preferably from 1.5 to 7.5 mg/kg/day.

An initial oral dose of cyclic oligopeptide cyclosporine microparticles of the current invention can be given up to 12 hours prior to a transplantation, preferably as a single dose of up to about 15 mg/kg. The initial single daily dose can be continued postoperatively for up to about two weeks and can then be tapered by about 5% per week to a maintenance dose of about 3–10 mg/kg/day.

Cyclic oligopeptide cyclosporine in the microparticles of the current invention can be used alone or in combination with azathioprine and corticosteroids, for example in the prophylaxis of organ rejection in kidney, liver, and heart allogeneic transplants. Cyclic oligopeptide cyclosporine in the microparticles of the current invention can also be used for the treatment of patients with severe active rheumatoid arthritis alone or in combination with methotrexate in rheumatoid arthritis patients who do not respond adequately to methotrexate alone.

By industrially useful insoluble or poorly soluble compounds we include biologically useful compounds, imaging agents, pharmaceutically useful compounds and in particular drugs for human and veterinary medicine, and most preferably solid cyclic oligopeptide cyclosporine. Water-insoluble compounds are those having a poor solubility in water, that is, less than 5 mg/ml at a physiological pH of 6.5 to 7.4, although the water solubility may be less than 1 mg/ml and even less than 0.1 mg/ml.

Examples of some preferred water-insoluble drugs include immunosuppressive agents such as cyclic oligopeptide cyclosporines including cyclosporine (cyclosporin A), immunoactive agents, antiviral and antifungal agents, antineoplastic agents, analgesic and anti-inflammatory agents, antibiotics, anti-epileptics, anesthetics, hypnotics, sedatives, antipsychotic agents, neuroleptic agents, antidepressants, anxiolytics, anticonvulsant agents, antagonists, neuron blocking agents, anticholinergic and cholinomimetic agents, antimuscarinic and muscarinic agents, antiadrenergic and antiarrhythmics, antihypertensive agents, antieoplastic agents, hormones, and nutrients. A detailed description of these and other suitable drugs may be found in *Remington's Pharmaceutical Sciences*, 18th edition, 1990, Mack Publishing Co. Philadelphia, Pa.

The phospholipid may be a natural or synthetic phospholipid, for example phosphatidylcholine, phosphatidylethanolamine, phosphatidylserine, phosphatidylinositol, phosphatidylglycerol, phosphatidic acid, lysophospholipids, egg or soybean phospholipid, purified or enriched fractionated or partially purified extracts of natural phospholipids such as purified or enriched or fractionated or partially purified egg derived phospholipids, Lipoid E80, or a combination thereof. The phospholipid may be salted or desalted, hydrogenated or partially hydrogenated or natural semisynthetic or synthetic. Examples of commercially available phospholipids include but are not limited to egg phospholipids P123 (Pfanstiehl), Lipoid E80 (Lipoid); and hydrogenated soy phospholipids Phospholipon 90H and 100H (Natterman) and 99% pure soy phosphatidyl choline (Avanti Polar Lipids).

In one aspect, the phospholipid can be selected from the group consisting of phospholipid of egg origin, phospholipid of plant origin, a semisynthetic phospholipid, a synthetic phospholipid, a phospholipid in partly hydrogenated form, a phospholipid in fully hydrogenated form, a phospholipid in desalted form, a phospholipid salt, phosphatidylcholine, dimyristoyl phosphatidylglyerol sodium salt, phosphatidylethanolamine, phosphatidylserine, phosphatidic acid, a lysophospholipid, or a combination thereof.

Suitable second surface modifiers can be selected from the group consisting of natural surfactants, nonionic surfactants, anionic surfactants, cationic surfactants, and colloidal clays.

In one aspect, examples of some suitable second surface modifiers include: (a) natural surfactants such as casein, gelatin, tragacanth, waxes, enteric resins, paraffin, acacia, gelatin, cholesterol esters and triglycerides, (b) nonionic surfactants such as polyoxyethylene fatty alcohol ethers, sorbitan ethers, sorbitan fatty acid esters, polyoxyethylene fatty acids esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, polyvinylpyrrolidone, and synthetic phospholipids, (c) anionic surfactants such as potassium laurate, triethanolamine stearate, sodium lauryl sulfate, alkyl polyoxyethylene sulfates, sodium alginate, dioctyl sodium sulfosuccinate, negatively charged phospholipids (phosphatidyl glycerol, phosphatidyl inosite, phosphatidylserine, phosphatidic acid and their biocompatible salts), and negatively charged glyceryl esters, sodium carboxymethylcellulose, and calcium carboxymethylcellulose, (d) cationic surfactants such as quaternary ammonium compounds, benzalkonium chloride, cetyltrimethylammonium bromide, chitosans and lauryldimethylbenzylammonium chloride, (e) colloidal clays such as bentonite and veegum or a combination thereof. A detailed description of these surfactants may be found in Remington's Pharmaceutical Sciences, and Theory and Practice of Industrial Pharmacy, Lachman et al, 1986.

In another aspect, suitable second surface modifiers include can be selected from the group consisting of (a) natural surfactants including casein, gelatin, tragacanth, waxes, enteric resins, paraffin, acacia, gelatin, cholesterol esters and triglycerides, (b) nonionic surfactants including polyoxyethylene fatty alcohol ethers, sorbitan ethers, sorbitan fatty acid esters, polyoxyethylene fatty acids esters, sorbitan esters, glycerol monostearate, polyethylene glycols, cetyl alcohol, cetostearyl alcohol, stearyl alcohol, poloxamers, polaxamines, methylcellulose, hydroxycellulose, hydroxy propylcellulose, hydroxy propylmethylcellulose, noncrystalline cellulose, polyvinyl alcohol, and polyvinylpyrrolidone, (c) anionic surfactants including potassium laurate, triethanolamine stearate, sodium lauryl sulfate, alkyl polyoxyethylene sulfates, sodium alginate, dioctyl sodium sulfosuccinate, negatively charged glyceryl esters, sodium carboxymethylcellulose, and calcium carboxymethylcellulose, (d) cationic surfactants including quaternary ammonium compounds, benzalkonium chloride,. cetyltrimethylammonium bromide, chitosans and lauryldimethylbenzylammonium chloride, and (e) colloidal clays such as bentonite and veegum, or a combination thereof.

In still another aspect of this invention, the second surface modifier can be selected from the group of negatively charged phospholipids, for example negatively charged phospholipids consisting of phosphatidyl glycerol, phosphatidyl inosite, phosphatidylserine, phosphatidic acid and their salts. A preferred charged phospholipid in this aspect is dimyristoyl phosphatidylglycerol sodium salt.

In yet another aspect of this invention, phospholipids are not included in the group consisting of second surface modifiers, i.e., the second surface modifier is not a phospholipid.

More specifically, examples of suitable second surface modifiers include one or combination of the following surfactants: polaxomers, such as Pluronic™ F68, F108, and F127, which are block copolymers of ethylene oxide and propylene oxide available from BASF, and poloxamines, such as Tetronic™ 908 (T908), which is a tetrafunctional block copolymer derived from sequential addition of ethylene oxide and propylene oxide to ethylenediamine available from BASF, Triton™ X-200, which is an alkyl aryl polyether sulfonate, available from Rohm and Haas. Tween 20, 40, 60 and 80, which are polyoxyethylene sorbitan fatty acid esters, available from ICI Specialty Chemicals, polyoxyethylene stearate (Myri 52) available from ICI Specialty Chemicals, Carbowax™ 3550 and 934, which are polyethylene glycols available from Union Carbide, hydroxy propylmethylcellulose, sodium dodecylsulfate, sodium deoxycholate, and cetyltrimethylammonium bromide.

In some cases preferably at least two second surfactants are used. When two second surfactants or surface modifiers (for example, a primary second surface modifier and a secondary second surface modifier) are used in addition to a phospholipid to stabilize the particles, the ratio of the primary and secondary second surface modifiers can range from about 1 part of said primary second surface modifier to 999 parts of said secondary second surface modifier to about 999 parts of said primary second surface modifier to 1 part of said secondary second surface modifier, preferably from about 1 part of said primary second surface modifier to 99 parts of said secondary second surface modifier to about 99 parts of said primary second surface modifier to 1 part of said secondary second surface modifier, more preferably from about 1 part of said primary second surface modifier to 9 parts of said secondary second surface modifier to about 9 parts of said primary second surface modifier to 1 part of said secondary second surface modifier. Up to and including equal amounts of primary and secondary surface modifiers can be used. In another aspect more than two secondary surface modifiers can be used wherein the ratio of any two is in the just described distribution of ratios, up to and including equal amounts of each. The ratio of phospholipid to total amount of secondary surface modifier(s) can range from about 100:1 to about 1:1, preferably from about 10:1 to about 2:1. The ratio of drug to phospholipid can range from 1:10 to about 10:1, preferably from 1:5 to about 5:1. Drug concentrations in the formulation can range from about 1% to about 90%, preferably about 2% to about 20%, and more preferably from about 2% to about 10% of the formulation. An especially preferred drug concentration is 5%.

In a preferred aspect of the invention, when free-flowing formulations are desired, the second surfactant(s) or surface modifier(s) will itself be a powder. In one aspect of the invention, preferred second surface modifiers include one or more members of the group consisting of Tween 80, Tween 20, Pluronic F68, Tetronic T908, Myri 52, sodium deoxycholate, and combinations thereof. In another aspect of the invention, preferred surface modifiers include one or more members of the group consisting of Tween 80, Tween 20, Pluronic F68, Tetronic T908, Myri 52, cetyl trimethylammonium bromide, and combinations thereof.

While we do not wish to be held to a particular theory, it is thought that some of the functions of the second surface modifier(s) as it relates to this invention are (a) suppressing the process of Ostwald ripening and therefore maintenance of the particle size of the solid cyclic oligopeptide cyclosporine; (b) increasing the storage stability, minimizing sedimentation, and decreasing the particle growth during lyophilization and reconstitution of the solid cyclic oligopeptide cyclosporine particles; (c) adhering or coating firmly onto the surfaces of water-insoluble drug particles which particles contain solid cores of drug, particularly water-insoluble solid cyclic oligopeptide cyclosporine, and therefore modifying the interfaces between the particles and the liquid in the resulting formulations; (d) increasing the interface compatibility between water-insoluble solid drug particles and the liquid, particularly between water-insoluble solid cyclic oligopeptide cyclosporine particles and the liquid; (e) possibly orienting preferentially themselves with the hydrophilic portion sticking into the aqueous solution and the lipophilic portion strongly adsorbed at the water-insoluble solid cyclic oligopeptide cyclosporine drug particle surfaces.

In another aspect of this invention, there is provided a pharmaceutical composition of particles of cyclic oligopeptide cyclosporine produced by applying energy to solid cyclic oligopeptide cyclosporine in the presence of one or more phospholipids and one or more surface modifier(s), wherein each particle consists essentially of a solid cyclic oligopeptide cyclosporine core stabilized by a combination of one or more phospholipids and one or more surface modifier(s) adhering to or coated on the surface of the core, wherein the surface modifier(s) provide volume-weighted mean particle size values of solid cyclic oligopeptide cyclosporine about 50% smaller than particles produced in the presence of a phospholipid and without the presence of the surface modifier(s) using the same energy input, and wherein said particles of solid cyclic oligopeptide cyclosporine when administered orally in a pharmaceutically acceptable dosage form to a fasted patient in need of treatment by cyclic oligopeptide cyclosporine provide an amount of cyclic oligopeptide cyclosporine effective in immunosuppressive therapy that is within 80% of the amount provided by said dosage form when administered orally to a patient in need of treatment by cyclic oligopeptide cyclosporine fed a low fat meal.

In another aspect of this invention, there is provided a pharmaceutical composition of particles of solid cyclic oligopeptide cyclosporine produced by applying energy to solid cyclic oligopeptide cyclosporine in the presence of one or more phospholipids and one or more surface modifier(s), wherein each particle consists essentially of a solid cyclic oligopeptide cyclosporine core stabilized by a combination of one or more phospholipids and one or more surface modifier(s) adhering to or coated on the surface of the core, wherein the surface modifier(s) provide volume-weighted mean particle size values of solid cyclic oligopeptide cyclosporine about 50% smaller than particles produced in the presence of a phospholipid and without the presence of the surface modifier(s) using the same energy input, and wherein said particles of solid cyclic oligopeptide cyclosporine when administered orally in a pharmaceutically acceptable dosage form to a fasted patient in need of treatment by cyclic oligopeptide cyclosporine provide an amount of cyclic oligopeptide cyclosporine effective in immunosuppressive therapy that is within 90% of the amount provided by said dosage form when administered orally to a patient in need of treatment by cyclic oligopeptide cyclospqrine fed a high fat meal.

As used herein, the phrase "one or more surface modifier (s)" is also intended to mean "one or more surface modifier."

Pharmaceutically acceptable dosage forms that comprise a pharmaceutical composition of particles of solid cyclic oligopeptide cyclosporine produced by applying energy to solid cyclic oligopeptide cyclosporine in the presence of one or more phospholipids and one or more surface modifier(s), wherein each particle consists essentially of a solid cyclic oligopeptide cyclosporine core stabilized by a combination of one or more phospholipids and one or more surface modifier(s) adhering to or coated on the surface of the core, wherein the surface modifier(s) provide volume-weighted mean particle size values of solid cyclic oligopeptide cyclosporine about 50% smaller than particles produced in the presence of a phospholipid and without the presence of the surface modifier(s) using the same energy input include tablets, capsules, suspensions, lozenges, pills and the like suitable for oral administration to a patient in need of treatment by cyclic oligopeptide cyclosporine. Dosage forms may contain additional excipients such as carbohydrates, sugars, binders, cryoprotectants, silica, release agents, magnesium stearate, gelatin, and other ingredients well known in the art of tablet and capsule making.

The unexpected reduction and obviation of the difference between uptake of cyclic oligopeptide cyclosporine in the presence and absence of food can be considered in view of the currently available dosage formulations which exhibit variability in fasted versus fed cyclic oligopeptide cyclosporine uptake. These currently available formulations are known to contain inactive ingredients such corn oil, olive oil, gelatin, glycerol, Labrafil M 2125 CS (polyoxyethlylated glycolysed glycerides), Labrafil M 1944 CS (polyoxyethylated oleic glycerides), sorbitol, and Cremophor EL (polyoxyethylated castor oil). In the particles of the current invention, the reduction and obviation of the difference between uptake of cyclic oligopeptide cyclosporine in the presence and absence of food is uniquely related to the presence of the combination of phospholipid(s) and surface modifier(s) adhering to a solid core of cyclic oligopeptide cyclosporine in the particles. The combination of phospholipid(s) and surface modifier(s) provide small particles of cyclic oligopeptide cyclosporine while at the same time dampening the difference with respect to uptake of cyclic oligopeptide cyclosporine between the fed and fasted state. Preferably this difference in levels of cyclic oligopeptide cyclosporine uptake as a function of the presence or absence of food is less than 80% between fed and fasted states, more preferably less than 90%, and most preferably less than 95%.

Considerable variations as to the identities and types of phospholipid and especially the surface modifier(s) (surface active agent or a combination of two or more surface active agents) should be expected depending upon the drug, particularly upon cyclic peptide cyclosporine drug, or surface active agent(s) selected because the surface properties of the small particles of each drug are largely different from one another. The most advantageous surface active agent(s) for a drug, particularly for an insoluble cyclic peptide cyclosporine drug, will be apparent following empirical tests to identify the second surfactant and phospholipid or second surfactant system in combination with phospholipid or combinations of phospholipids that provides the requisite particle size and particle size stability on storage over time.

Various procedures can be used to produce these stable sub-micron and micron size particles which contain a core of solid drug, particularly a core of solid cyclic peptide cyclosporine, and which are stabilized by a combination of phospholipid(s) and surface modifier(s). These procedures include mixing the insoluble substance, particularly the water-insoluble or poorly water-soluble solid cyclic oligopeptide cyclosporine, with one or more phospholipid(s) and one or more second surfactant(s) followed by sonication, milling, homogenization, and/or microfluidization; or precipitating from a solution of the substance, particularly the water-insoluble or poorly water-soluble solid cyclic oligopeptide cyclosporine, using antisolvent and solvent precipitation in the presence of phospholipid and second surfactant(s). Mannitol and other agents may be added to adjust the final formulation to isotonicity as well as to act as a stabilizing aid during drying.

Unless otherwise specified, all parts and percentages reported herein are weight per unit volume (w/v), in which the volume in the denominator represents the total volume of the system. Diameters of dimensions are given in millimeters (mm=$10^{-3}$ meters), micrometers ($\mu$m=$10^{-6}$ meters), nanometers (nm=$10^{-9}$ meters) or Angstrom units (=0.1 nm). Volumes are given in liters (L), milliliters (mL=$10^{-3}$ L) and microliters ($\mu$L=$10^{-6}$ L). Dilutions are given by volume. All temperatures are reported in degrees Celsius. The compositions of the invention can comprise, consist essentially of, or consist of the materials set forth and the process or method can comprise, consist essentially of, or consist of the steps set forth with such materials.

EXAMPLES

The following examples further explain and illustrate the invention and are not meant to be limiting to the scope of the invention.

Example 1

Microparticles of a Solid ore of Cyclic Oligopeptide Cyclosporine Stabilized with a Coating of Phospholipid and a Second Surface Active Agent.

Microparticles of cyclic oligopeptide cyclosporine, an immunosuppressive drug, were prepared as follows. The composition and concentration of excipients of the microparticle cyclic oligopeptide cyclosporine formulation are listed below:

| | |
|---|---|
| Cyclic oligopeptide cyclosporine (solid in the core of the particles) | 50 mg/ml |
| Egg Phosphatidylcholine | 100 mg/ml |
| Mannitol | 55 mg/ml |
| Tween 80 | 10 mg/ml |
| Distilled Water | qs to 100% |
| Total Volume | 20 ml |

Solid cyclic oligopeptide cyclosporine with an average particle size from 5–100 $\mu$m, and mannitol were purchased from Sigma, egg phosphatidylcholine was produced by Pfanstiehl, Tween 80 was purchased from ICI.

The above components were placed in a 30 ml beaker and pre-mixed with a hand-held biohomogenizer (Honeywell DR 4200 model GP) for 1–5 min. During homogenization, dilute NaOH was added to the pre-mix to adjust the pH from 3.1 to 7±0.5. The pre-mix was placed in a water-jacketed vessel (50 ml capacity) through which thermostated water at 4° C. was circulated to control the temperature of the formulation. The pre-mix was subjected to high shear energy of a probe sonicator (Fisher, model 550 Sonic Dismembrator) with a 0.5 inch diameter probe. Sonic pulses of 10 seconds at 10-second intervals at a power setting of 5 were utilized. During sonication the temperature of the formulation was 18±2° C. and the cyclosporine remained a solid. The pH during sonication was adjusted to 7±0.5 with dilute NaOH. Total sonication time employed to prepare the microparticle cyclic oligopeptide cyclosporine that consists of a core of solid cyclic oligopeptide cyclosporine was usually 10.5 hours or less. The microparticle-cyclic oligopeptide cyclosporine formulation was placed in 20 ml vials and stored at 4 and 25° C. for further stability studies.

Particle size distribution of the suspension was analyzed with a NICOMP model 370 Particle Size Analyzer. This instrument utilizes photon correlation spectroscopy for particle sizing in the submicron region. A small volume of the suspension of solid cyclic oligopeptide cyclosporine microparticles was diluted with water and placed in the cell of the particle size analyzer. Particle size determination based on volume weighted and number weighted particle size determination of the suspension, represented as a Gaussian distribution by the NICOMP 370 software, yielded the mean particle size values at days 0, 7, and 51, which are listed below in Table I.

TABLE I

Volume- and Number-Weighted Particle Size Stability of Microparticle-Cyclic Oligopeptide Cyclosporine

| | Storage at 4° C. Mean Particle Size (nm) | | Storage at 25° C. Mean Particle Size (nm) | |
|---|---|---|---|---|
| Storage Time Days | Volume-Weighted | Number-Weighted | Volume-Weighted | Number-Weighted |
| 0 | 461 | 63 | 361 | 63 |
| 7 | 337 | 69 | 423 | 67 |
| 51 | 358 | 76 | 455 | 66 |

Approximately 20 $\mu$of the freshly prepared suspension of solid cyclic oligopeptide cyclosporine microparticles consisting of solid cores of solid cyclic oligopeptide cyclosporine was placed on a clean slide, with a clean cover glass, and examined under an Olympus BH2 microscope with 1000× magnification. An eyepiece equipped with a graticule was used to estimate the particle size. Most of the particles in the suspension were 0.3 to 0.5 $\mu$m. Furthermore, microscopic examination of the suspension confirmed non-agglomerated or flocculated micron and sub-micron size cyclic oligopeptide cyclosporine drug particles exhibiting Brownian motion.

Example 2

Comparative Preparation of Particles of Solid Core of Cyclic Oligopeptide Cyclosporine Using Phospholipid Alone.

For purpose of comparison (not according to the invention) using only a phoapholipid, microparticle-cyclic oligopeptide cyclosporine with lecithin alone (without the second surface modifier, Tween 80) was also prepared using the same procedure as Example 1. The suspension was stored in 20 ml glass vials for storage stability studies. The volume and number weighted mean particle size values of the suspension stored at 4 and 25° C. are listed below. The results in Table II illustrate for times day 0, day 1 and day 6 that the presence of lecithin alone (without the presence of a second surface modifier such as Tween 80) does not provied the particle size reduction and enhancement in storage stability as describe in Example 1.

TABLE II

Volume-Weighted Particle Size Stability of Microparticle-Cyclic Oligopeptide Cyclosporine Prepared with Phospholipid in the Absence of a Second Surfactant

| Storage Time Days | Storage at 4° C. Mean Particle Size (nm) | | Storage at 25° C. Mean Particle Size (nm) | |
|---|---|---|---|---|
| | Volume-Weighted | Number-Weighted | Volume-Weighted | Number-Weighted |
| 0 | 704 | 91 | 704 | 91 |
| 1 | 1472 | 503 | 2230 | 755 |
| 6 | 1740 | 416 | 2290 | 874 |

Example 3

Preparation and Volume- and Number-weighted Particle Size Stability Data of Microparticle-cyclic Oligopeptide Cyclosporine Prepared in the Absence of Phospholipid using Tween 80.

For purpose of comparison (not according to the invention) using only a surface modifier, microparticle-cyclic oligopeptide cyclosporine with Tween 80 alone (without a phospholipid, egg phosphatidylcholine) was also prepared using the same procedure as Example 1. The suspension was stored in 20 ml glass vials. The results in Table III illustrate that the presence of Tween 80 alone (without the presence of phospholipid) does not provide particle size reduction as in Example 1.

TABLE III

Volume- and Number-Weighted Particle Size Stability of Microparticle-Cyclic Oligopeptide Cyclosporine

| | Mean Particle Size (nm) | |
|---|---|---|
| Days | Volume-Weighted | Number-Weighted |
| 0 | 521 | 67 |

Example 4 Microparticle-Docosanol Formulations

The following microparticle-Docosanol formulations were prepared by the process of the invention with Tween 80, Tween 20, egg phosphatidylcholine, and/or Phospholipon 90H as surface modifiers. Docosanol is available from Sigma. The formulations were prepared according to the procedures of Example 1. The compositions and concentration of excipients of the microparticle formulations are listed below as examples 4.1 (comparative), 4.2, 4.3, 4.4 and 4.5 (comparative). The energy input in each of the examples 4.1 to 4.5 was the same within experimental error, i.e., the energy input in each of the examples 4.1 to 4.5 was substantially the same.

Example 4.1 Microparticle-Docosanol (comparative)

| Docosanol | 20 mg/ml |
|---|---|
| Egg Phosphatidylcholine | 50 mg/ml |
| Mannitol | 55 mg/ml |
| Distilled Water | qs to 100% |
| Total Volume | 20 ml |

Example 4.2 Microparticle-Docosanol

| Docosanol | 20 mg/ml |
|---|---|
| Egg Phosphatidylcholine | 50 mg/ml |
| Mannitol | 55 mg/ml |
| Tween 80 | 10 mg/ml |
| Distilled Water | qs to 100% |
| Total Volume | 20 ml |

Example 4.3 Microparticle-Docosanol

| Docosanol | 20 mg/ml |
|---|---|
| Egg Phosphatidylcholine | 50 mg/ml |
| Mannitol | 55 mg/ml |
| Tween 20 | 10 mg/ml |
| Distilled Water | qs to 100% |
| Total Volume | 20 ml |

Example 4.4 Microparticle-Docosanol

| Docosanol | 20 mg/ml |
|---|---|
| Phospholipon 90H | 30 mg/ml |
| Mannitol | 55 mg/ml |
| Tween 80 | 10 mg/ml |
| Distilled Water | qs to 100% |
| Total Volume | 20 ml |

Example 4.5 Microparticle-Docosanol (comparative)

| Docosanol | 20 mg/ml |
|---|---|
| Mannitol | 55 mg/ml |
| Tween 80 | 10 mg/ml |
| Distilled Water | qs to 100% |
| Total Volume | 20 ml |

The mean volume- and number-weighted particle size values of the suspension were 286 nm, and 98 nm, respectively.

The volume-weighted mean particle size values of the above suspension stored at 4° C. are listed below in Table IV.

TABLE IV

Volume-Weighted and Number-Weighted Particle Size Stability of Microparticle-Docosanol Stored at 4° C.

| Storage Time Days | Mean Particle Size (nm) | | Mean Particle Size (nm) | |
|---|---|---|---|---|
| | Volume-Weighted | Number-Weighted | Volume-Weighted | Number-Weighted |
| | (Example 4.1 comparative) | | (Example 4.2) | |
| 0 | 688 | — | 112 | 55 |
| 30 | ND | ND | 156 | 81 |
| | (Example 4.3) | | (Example 4.4) | |
| 0 | 129 | 61 | 90 | 35 |
| 30 | 184 | 99 | 127 | 39 |

ND = Not Determined

The data in Table IV illustrate that much smaller particles are produced in the present invention when a second surfactant in addition to a phospholipid are used in the preparation of particle relative to when phospholipid alone is used. The data in Table IV illustrate that these particles retain their particle size over time without significant increase in size.

Example 5
Microparticle-RTP-4055 (An Antiviral Drug)

The following seven microparticle-RTP-4055 (an antiviral drug) formulations were prepared with combinations of Tween 80, Tetronic 908, Pluronic F-68, egg phosphatidylcholine, and/or phospholipon 90H as surface modifiers. The details of the sonication method are similar to those discussed in Example 1. The composition and concentration of excipients of the microparticle formulations are listed below:

Example 5.1 Microparticle-RTP-4055 (comparative)

| | |
|---|---|
| RTP-4055 | 50 mg/ml |
| Egg Phosphatidylcholine | 50 mg/ml |
| Distilled Water | qs to 100% |
| Total Volume | 25 ml |

The mean volume weighted particle size of the suspension of example 5.1 was 3195 nm.

Example 5.2 Microparticle-RTP-4055

| | |
|---|---|
| RTP-4055 | 50 mg/ml |
| Egg Phosphatidylcholine | 50 mg/ml |
| Mannitol | 55 mg/ml |
| Pluronic F-68 | 5 mg/ml |
| Distilled Water | qs to 100% |
| Total Volume | 25 ml |

The mean volume- and number-weighted particle size values of the suspension of example 5.2 were 672 nm and 76 nm respectively.

Example 5.3 Microparticle-RTP-4055

| | |
|---|---|
| RTP-4055 | 50 mg/ml |
| Egg Phosphatidylcholine | 50 mg/ml |
| Mannitol | 55 mg/ml |
| Tetronic 908 | 5 mg/ml |
| Distilled Water | qs to 100% |
| Total Volume | 25 ml |

The mean volume- and number-weighted particle size values of the suspension of example 5.3 were 436 nm and 59 nm respectively.

Example 5.4 Microparticle-RTP-4055 (Comparative)

| | |
|---|---|
| RTP-4055 | 50 mg/ml |
| Phospholipon 90H | 30 mg/ml |
| Distilled Water | qs to 100% |
| Total Volume | 25 ml |

The mean volume- and number-weighted particle size values of the suspension of example 5.4 were 1117 nm and 108 nm respectively.

Example 5.5 Microparticle-RTP-4055

| | |
|---|---|
| RTP-4055 | 50 mg/ml |
| Phospholipon 9011 | 30 mg/ml |
| Mannitol | 55 mg/ml |
| Dimyristoylphosphatidyl choline (DMPG) | 3 mg/ml |
| Tween 80 | 10 mg/ml |
| Distilled Water | qs to 100% |
| Total Volume | 25 ml |

The mean volume weighted particle size of the suspension of example 5.5 was 236 nm. The mean volume weighted particle size of the suspension stored at 4° C. for 1 week and 1 month are 328 and 397 nm, respectively, which indicates the stability of the suspension.

Example 5.6 Microparticle-RTP-4055

| | |
|---|---|
| RTP-4055 | 50 mg/ml |
| Phospholipon 90H | 30 mg/ml |
| Mannitol | 55 mg/ml |
| Tween 80 | 10 mg/ml |
| Distilled Water | qs to 100% |
| Total Volume | 25 ml |

The mean volume- and number-weighted mean particle size values of the suspension of example 5.6 were 382 nm and 59 nm respectively. Within the error limits, there was no variation in the mean particle size after one week of storage at 4° C.

Example 5.7 Microparticle-RTP-4055 (Comparative)

| | |
|---|---|
| RTP-4055 | 50 mg/ml |
| Mannitol | 55 mg/ml |
| Tween 80 | 10 mg/ml |
| Distilled Water | qs to 100% |
| Total Volume | 25 ml |

The mean volume- and number-weighted mean particle size values of the suspension of example 5.7 were 545 nm, and 75 nm, respectively, and within the error limits, there was no variation in the mean particle size after one week of storage at 4° C.

Example 6
Microparticle-Piroxicam Formulations

The following six microparticle-Piroxicam formulations were prepared with combination of Tween 80, Tetronic 908, Pluronic F-68, and/or egg phosphatidylcholine as surface modifiers. Piroxicam was received from Cipla. The details of the sonication method are similar to those discussed in Example 1. The compositions and concentration of excipients of the microparticle formulations are listed below:

Example 6.1 Microparticle-Piroxicam

| Piroxicam | 67 mg/ml |
|---|---|
| Egg Phosphatidylcholine | 67 mg/ml |
| Mannitol | 67 mg/ml |
| Tween 80 | 5 mg/ml |
| Tetronic 908 | 5 mg/ml |
| Distilled Water | qs to 100% (w/v) |
| Total Volume | 15 ml |

The mean volume- and number-weighted particle size values of the suspension of example 6.1 were 674nm and 72 nm respectively.

Example 6.2 Microparticle-Piroxicam

| Piroxicam | 67 mg/ml |
|---|---|
| Egg Phosphatidylcholine | 67 mg/ml |
| Mannitol | 67 mg/ml |
| Tetronic 908 | 5 mg/ml |
| Distilled Water | qs to 100% (w/v) |
| Total Volume | 15 ml |

The mean volume- and number-weighted particle size values of the suspension of example 6.2 were 455 nm and 58 nm respectively.

Example 6.3 Microparticle-Piroxicam

| Piroxicam | 67 mg/ml |
|---|---|
| Egg Phosphatidylcholine | 67 mg/ml |
| Marinitol | 67 mg/ml |
| Pluronic F-68 | 5 mg/ml |
| Distilled Water | qs to 100% (w/v) |
| Total Volume | 15 ml |

The mean volume- and number-weighted particle size values of the suspension of example 6.3 were 564 nm and 68 nm respectively.

Example 6.4 Microparticle-Piroxicam

| Piroxicam | 67 mg/ml |
|---|---|
| Egg Phosphatidylcholine | 67 mg/ml |
| Mannitol | 67 mg/ml |
| Tween 80 | 5 mg/ml |
| Cetyltrimethylammonium bromide | 10 mg/ml |
| Distilled Water | qs to 100% (w/v) |
| Total Volume | 15 ml |

The mean volume- and number-weighted particle size values of the suspension of example 6.4 were 479 nm and 80 nm respectively.

Example 6.5 Microparticle-Piroxicam

| Piroxicam | 67 mg/ml |
|---|---|
| Egg Phosphatidylcholine | 67 mg/ml |
| Mannitol | 67 mg/ml |
| Cetyltrimethylammonium Bromide | 10 mg/ml |
| Distilled Water | qs to 100% (w/v) |
| Total Volume | 15 ml |

The mean volume- and number-weighted particle size values of the suspension of example 6.5 were 670 nm and 128 nm respectively.

Example 6.6 Microparticle-Piroxicam (Comparative)

| Piroxicam | 67 mg/ml |
|---|---|
| Mannitol | 67 mg/ml |
| Tween 80 | 5 mg/ml |
| Tetronic 908 | 5 mg/ml |
| Distilled Water | qs to 100% |
| Total Volume | 15 ml |

The mean volume- and number-weighted particle size values of the suspension of example 6.6 were 1184 nm and 385 nm respectively.

Examples 7–12. Microparticles of Solid Cyclic Oligopeptide Cyclosporine Consisting of a Solid Cyclic Oligopeptide Cyclosporine Core Prepared in a Microfluidizer.

Microparticles of solid cyclic oligopeptide cyclosporine consisting of a solid cyclic oligopeptide cyclosporine core were prepared in a microfluidizer (Microfluidics, Newton, Ma) to examine the presence or absence of second surfactant, (examples 7 and 8 vs 9, 10 and 11), the use of a phospholipid having a high phospholipidal choline content (9 vs. 10, 11) and mixtures of two solid second surfactants, (10 vs 11); amounts of ingredients are percent by weight, balance water. The solid cyclic oligopeptide cyclosporine remained undissolved and in the solid state throughout this process. The energy input was the same for each example.

| Example: | 7 | 8 | 9 | 10 | 11 Batch 1 | 12 |
|---|---|---|---|---|---|---|
| Cyclic oligopeptide cyclosporine (forming a solid core in the microparticles) | 5% | 5% | 5% | 5% | 5% | 5% |
| Pfanstiehl egg phospholipid | 10% | | 10% | | 10% | 10% |
| Phospholipon 100H | | 2% | | 2% | | |
| Tween 80 | | | 2% | 2% | | |
| Myri 52 | | | | | 1% | 2% |
| Sodium deoxycholate | | | | | 0.25% | |
| Mannitol | 5.5% | 5.5% | 5.5% | 5.5% | 5.5% | 5.5% |
| Mean volume weighted particle size (microns) | 3.34 | 13.57 | 1.14 | 0.64 | 0.74 | 0.75 |

Examples 7 and 8 are not according to the invention because they contain phospholipid but lack second surfactant(s). The relatively significantly larger particle size of particles of examples 7 and 8 reflects this fact.

In the above examples cyclic oligopeptide cyclosporine was purchased as a solid from North China Pharmaceutical Corporation. P123 egg phospholipid (i.e., Pfanstiehl P123 or Pfanstiehl egg phospholipid) is a waxy substance and contains about 70% phosphatidylcholine while Phospholipon 100H (Natterman) is hydrogenated soy lecithin, a powder, and contains greater than 90% phosphatidylcholine. Tween 80 was purchased from ICI; Myrj 52 was purchased from ICI; and sodium deoxycholate was purchased from Perdotti Chimici E. Alimentari S.P.A.

The formulation of Example 9 is the same as that of Example 1 but was produced using a microfluidizer rather than by sonication.

We have found that purer lipids tend to be less susceptible to hydrolysis (dehydration). In addition, Phospholipon 100H is a free flowing powder while Pfanstiehl P123 is a waxy substance. Formulations containing Pfanstiehl P123 did not always form free flowing powders.

Tween 80 is a viscous liquid. Upon lyophilization formulations containing Tween 80 each produced a powder having a slightly sticky touch. Such formulations did not always form suitably free flowing powders. However, Myrj 52 and sodium deoxycholate, both solids, did produce free flowing powders.

Sodium deoxycholate is a bile salt. Absorption of cyclosporine products can be dependent upon solubilization by bile salts. Thus uptake of cyclic oligopeptide cyclosporine may be enhanced by sodium deoxycholate.

The combination of two second surfactants together with a phospholipid can unexpectedly enhance the reduction of particle size, increase particle size stability, and enhance manufacturability of a formulation of particles of solid cyclic oligopeptide cyclosporine in a core stabilized by the combination of two second surfactants together with a phospholipid. Thus, in Example 11, the combination of two second surfactants, Myri 52 and sodium deoxycholate, together with an egg phospholipid, Pfanstiehl egg phospholipid, was found to unexpectedly enhance the reduction of particle size, increase particle size stability, and thus potentially enhance the manufacturability of a formulation of particles of solid cyclic oligopeptide cyclosporine in a core stabilized by the combination of the two second surfactants together with the phospholipid.

The product of Example 11 (batch 2) remained stable on storage. For example, at initial time 0 the particle size was 0.92 $\mu$m, and after 4 months the particle size was 0.95 $\mu$m.

Comparison of the volume weighted mean particle size of particles of solid cyclic oligopeptide cyclosporine in examples 9 and 7 shows a ratio of 1.14/3.34. Thus, the particles of solid cyclic oligopeptide cyclosporine of example 9 prepared with phospholipid together with a second surfactant, Tween 80, are unexpectedly more than 50% smaller than the particles of solid cyclic oligopeptide cyclosporine prepared with phospholipid alone without the presence of the second surfactant using the same energy input.

Comparison of the volume weighted mean particle size of particles of solid cyclic oligopeptide cyclosporine in examples 10 and 8 shows a ratio of 0.64/13.57. Thus, the particles of solid cyclic oligopeptide cyclosporine of example 10 prepared with phospholipid together with a second surfactant, Tween 80, are unexpectedly more than 50% smaller than the particles of solid cyclic oligopeptide cyclosporine prepared with phospholipid alone without the presence of the second surfactant using the same energy input.

Comparison of the volume weighted mean particle size of particles of solid cyclic oligopeptide cyclosporine in examples 11 and 7 shows a ratio of 0.74/3.34. Thus, the particles of solid cyclic oligopeptide cyclosporine of example 11 prepared with phospholipid together with two second surfactants, Myri 52 and sodium deoxycholate, are unexpectedly more than 50% smaller than the particles of solid cyclic oligopeptide cyclosporine prepared with phospholipid alone without the presence of the second surfactants using the same energy input.

Example 13

Bioavailability of Solid Cyclic Oligopeptide Cyclosporine Particles of this Invention Relative to Neoral® Capsules of Microemulsion Bioavailability of various suspensions was assessed in male volunteers and values obtained were reported relative to Neoral® capsules of microemulsion (Novartis). Results are as follows:

| | Example 9 | Example 11 | Example 12* |
|---|---|---|---|
| $AUC_{0\text{-}inf}$ | 0.97 | 0.91 | 0.86 |
| Cmax | 0.79 | 0.84 | 0.84 |
| Particle Size** | 0.67 micron | 1.35 micron**** | 0.75 micron |
| Particle Size*** | 0.58 micron | 0.47 micron | 0.72 micron |

*Example 12 = Example 11 but modified to include 2% Myri 52 and no sodium deoxycholate
**Volume weighted particle size D[4,3]
***D50% value
****Process intentionally terminated at this particle size

What is claimed is:

1. A process of stabilizing solid cyclic oligopeptide cyclosporine microparticles, each microparticle consisting of a solid cyclic oligopeptide cyclosporine core, and preventing said microparticles from aggregating or flocculating by coating or adhering onto the surfaces of the solid cyclic oligopeptide cyclosporine core microparticles a mixture of a phospholipid together with at least one non-ionic, anionic or cationic second surface modifier, the process comprising the steps of:

a) mixing particles of solid cyclic oligopeptide cyclosporine with a phospholipid and at least one non-ionic, anionic or cationic second surface modifier, and thereafter;

b) applying energy to the mixture sufficient to produce volume-weighted mean particle size values of said solid cyclic oligopeptide cyclosporine core microparticles about 50% smaller than particles produced without the presence of the second surface modifier using the same energy input.

2. The process of claim 1, wherein the phospholipid is selected from the group consisting of phospholipid of egg origin, phospholipid of plant origin, partly hydrogenated phospholipid, fully hydrogenated phospholipid, lysophospholipid, and combinations thereof.

3. The process of claim 1, wherein the phospholipid is selected from the group consisting of phosphatidylcholine, dimyristoyl phosphatidylglyerol sodium salt, phosphatidylethanolamine, phosphatidi ylserine, phosphatidic acid, and combinations thereof.

4. The process of claim 1, wherein the second surface modifier is selected from the group consisting of a polyoxyethylene sorbitan fatty acid ester polyoxyethylene stearate, a block copolymer of ethylene oxide and propylene oxide, a tetrafunctional block copolymer derived from sequential addition of ethylene oxide and propylene oxide to ethylenediamine, an alkyl aryl polyether sulfonate, polyethylene glycol, hydroxy propylmethylcellulose, sodium dodecylsulfate, sodium deoxycholate, cetyltrimethylammonium bromide, and combinations thereof.

5. The process of claim 1, wherein at least two second surface modifiers are used.

6. The process of claim 1, wherein the second surface modifier is present above the critical micelle concentration.

7. A pharmaceutical composition comprising microparticles prepared by the process of claim 1.

8. The pharmaceutical composition of claim 7, wherein each microparticle consists essentially of a solid cyclic oligopeptide cyclosporine core, said core coated and stabilized with a combination of phospholipid and at least one second surface modifier.

9. The pharmaceutical composition of claim 8, wherein the cyclosporine is cyclosporine A.

10. The pharmaceutical composition of claim 8 for oral, inhalation, ocular, nasal or injectable administration.

11. The pharmaceutical composition of claim 8 in injectable form for intravenous, intra-arterial, intramuscular, intradermal, subcutaneous, intra-articular, cerebrospinal, epidural, intracostal, intraperitoneal, intratumor, intrabladder, intra-lesion or subconjunctival administration.

12. A hard or soft gel capsule formulation comprising the pharmaceutical composition of claim 8.

13. A suspension spray-dried powder, lyophilized powder, granules, cream, ointment, suppository, pill, capsule or tablet containing the pharmaceutical composition of claim 8.

14. The pharmaceutical composition of claim 8, wherein the phospholipid is selected from the group consistmg of phospholipid of egg origin, phospholipid of plant origin, a synthetic phospholipid, a phospholipid in partly hydrogenated-form, a phospholipid in fully hydrogenated form, a phospholipid in desalted form, a phospholipid salt, a lysophospholipid, and combinations thereof with the proviso that the second surface modifier is not a phospholipid.

15. The pharmaceutical composition of claim 8, wherein the phospholipid is selected from the group consisting of phosphatidylcholine, dimyristoyl phosphatidylglyerol sodium salt, phosphatidylethanolamine, phosphatidylserine, phosphatidic acid, and combinations thereof with the proviso that the second surface modifier is not a phospholipid.

16. The pharmaceutical composition of claim 8, wherein the surface modifier is selected from the group consisting of a polyoxyethylene sorbitan fatty acid ester, a block copolymer of ethylene oxide and propylene oxide, polyoxyethylene stearate, a tetrafunctional block copolymer derived from sequential addition of ethylene oxide and propylene oxide to ethylenediamine, an alkyl aryl polyether sulfonate, polyethylene glycol, hydroxy propylmethylcellulose, sodium dodecylsulfate, sodium deoxycholate, cetyltrimethylammonium bromide, and combinations thereof.

17. The pharmaceutical composition of claim 8, wherein the surface modifier is an anionic phospholipid.

18. The pharmaceutical composition of claim 17, wherein the anionic phospholipid is selected from the group consisting of phosphatidyl glycerol, phosphatidyl inosite, phosphatidylserine, phosphatidic acid, and biocompatible salts thereof.

19. The pharmaceutical composition of claim 8, comprising at least two second surface modifiers.

20. The pharmaceutical composition of claim 8, wherein the second surface modifier is selected from the group consisting of a non-ionic surface modifier, an anionic surface modifier, and a cationic surface modifier.

21. The pharmaceutical composition of claim 8, wherein the second surface modifier is not a phospholipid.

22. The pharmaceutical composition of claim 8, which when administered orally in a pharmaceutically acceptable dosage form to a fasted patient in need of treatment by cyclic oligopeptide cyclosporine provides an amount of cyclic oligopeptide cyclosporine effective in immunosuppressive therapy that is within 80% of the amount of cyclosporine provided by said dosage form when administered orally to a patient in need of treatment by cyclic oligopeptide cyclosporine fed a low fat meal.

* * * * *